US009370774B2

(12) United States Patent
Kumar et al.

(10) Patent No.: US 9,370,774 B2

(45) **Date of Patent: *Jun. 21, 2016**

(54) HAND HELD MICRO PCR DEVICE INCLUDING MICROCONTROLLER FOR EXCHANGING INFORMATION WITH A COMMUNICATIONS INTERFACE

(75) Inventors: Kishore Krishna Kumar, Karnataka (IN); Raviprakash Jayaraman, Karnataka (IN); Sankaranand Kaipa Narasimha, Karnataka (IN); Renjith Mahiladevi Radhakrishnan, Karnataka (IN); Sathyadeep Viswanathan, Karnataka (IN); Chandrasekhar Bhaskaran Nair, Karnataka (IN); Pillarisetti Venkata Subbarao, Karnataka (IN); Manjula Jagannath, Karnataka (IN); Shilpa Chennakrishnaiah, Karnataka (IN); Sudip Mondal, Karnataka (IN); Venkatakrishnan Venkataraman, Karnataka (IN)

(73) Assignee: Bigtec Private Limited, Bangalore, Kamatake (IN)

( * ) Notice: Subject to any disclaimer, the term of this patent is extended or adjusted under 35 U.S.C. 154(b) by 432 days.

This patent is subject to a terminal disclaimer.

(21) Appl. No.: 12/682,555

(22) PCT Filed: Oct. 13, 2008

(86) PCT No.: PCT/IN2008/000665

§ 371 (c)(1), (2), (4) Date: Apr. 9, 2010

(87) PCT Pub. No.: WO2009/047804

PCT Pub. Date: Apr. 16, 2009

(65) Prior Publication Data

US 2010/0297640 A1 Nov. 25, 2010

(30) Foreign Application Priority Data

Oct. 12, 2007 (IN) ........................... 2311/CHE/2007
Oct. 12, 2007 (IN) ........................... 2312/CHE/2007
Oct. 12, 2007 (IN) ........................... 2313/CHE/2007
Oct. 12, 2007 (IN) ........................... 2314/CHE/2007
Oct. 15, 2007 (IN) ........................... 2328/CHE/2007

(51) Int. Cl.
*C12M 1/38* (2006.01)
*B01L 7/00* (2006.01)
*B01L 3/00* (2006.01)

(52) U.S. Cl.
CPC ................. *B01L 7/52* (2013.01); *B01L 3/5027* (2013.01); *B01L 2300/0627* (2013.01); *B01L 2300/0851* (2013.01); *B01L 2300/0887* (2013.01); *B01L 2300/16* (2013.01); *B01L 2300/1805* (2013.01)

(58) Field of Classification Search
USPC ................. 435/91.2, 287.2, 287.3, 288.7, 6.1
See application file for complete search history.

(56) References Cited

U.S. PATENT DOCUMENTS 4,010,133 A 3/1977 Nakayama
4,335,216 A 6/1982 Hodgkins et al.

(Continued)

OTHER PUBLICATIONS

Golonka (Sensors and Actuators B 111-112, 2005, p. 396-402).*

(Continued)

*Primary Examiner* — Michael Wilson

(74) *Attorney, Agent, or Firm* — Panitch Schwarze Belisario & Nadel LLP

(57) ABSTRACT

Instant invention is about a hand held micro PCR device comprising a LTCC micro PCR chip comprising a heater, a reaction chamber to load a sample. It also comprises a heater control to regulate the heater on basis of input received from a temperature sensor. It further has an optical system having an optical fiber to detect a fluorescence signal from the sample, and at least one communication interface to interact with other device(s).

7 Claims, 16 Drawing Sheets

(56) References Cited

U.S. PATENT DOCUMENTS

| | | | | |
|---|---|---|---|---|
| 5,708,570 | A | 1/1998 | Polinski, Sr. | |
| 5,801,108 | A | 9/1998 | Huang et al. | |
| 6,054,277 | A * | 4/2000 | Furcht et al. | 435/6.11 |
| 6,750,661 | B2 * | 6/2004 | Brooks et al. | 324/693 |
| 7,015,810 | B2 * | 3/2006 | Su | 340/539.11 |
| 2002/0191826 | A1 * | 12/2002 | Benett | B01L 7/52 382/129 |
| 2005/0145273 | A1 * | 7/2005 | Atwood | B01L 7/52 136/201 |
| 2005/0262031 | A1 * | 11/2005 | Saidi et al. | 706/21 |
| 2006/0166347 | A1 * | 7/2006 | Faulstich et al. | 435/259 |
| 2008/0125330 | A1 * | 5/2008 | Cady | B01L 3/502707 506/17 |

OTHER PUBLICATIONS

Sadler (IEEE Transactions on components and packaging technologies, Jun. 2003, vol. 26, No. 2, p. 309-316).*
Chou (Microelectronic Engineering, 61-62, 2002, p. 921-925).*
Kricka (Anal Bioanal Chem, 2003, vol. 377, p. 820-825).*
Northrop (Anal. Chem. 1998, vol. 70, p. 918-922).*
Northrup (Automation Technologies for genome characterization, John Wiley & Sons: New York 1997, Chapt. 9, p. 189-204).*
PCT International Search Report and Written Opinion, PCT/IN2008/000665, Apr. 3, 2009, 7 pages.
Golonka, L.J. et al. "LTCC Based Microfluidic System with Optical Detection," Sensors and Actuators B: Chemical, Nov. 2005, vol. 111-112, pp. 396-402.
Martinez-Cisneros, C.S. et al., "LTCC Microflow Analyzers with Monolithic Integration of Thermal Control," Sensors and Actuators A: Physical, Jul. 2007, vol. 138, No. 1, pp. 63-70.
Sadler, D.J. et al., "Thermal Management of BioMEMS: Temperature Control for Ceramic-Based PCR and DNA Detection Devices," IEEE Transaction on Components and Packaging Technologies, Jun. 2003, vol. 26, No. 2, pp. 309-316.
Jones, W.K. et al., "Chemical, Structural, and Mechanical Properties of the LTCC Tapes," The International Journal of Microcircuits and Electronic Packaging, 2000, pp. 469-473, vol. 23, No. 4.

* cited by examiner

HAND HELD MICRO PCR DEVICE INCLUDING MICROCONTROLLER FOR EXCHANGING INFORMATION WITH A COMMUNICATIONS INTERFACE

FIELD OF INVENTION

This invention relates to a portable real-time PCR system with disposable low temperature co-fired ceramics (LTCC) micro PCR chip. The invention further describes a method to control and monitor the micro-PCR and the apparatus involved for PCR.

BACKGROUND OF THE INVENTION

Over the past five years, research and development for clinical diagnostic systems based on lab-on-a-chip technologies have increased tremendously. Such systems hold great promise for clinical diagnostics. They consume sample material and reagents only in extremely low volumes. Individual small chips can be inexpensive and disposable. Time from sampling to result tends to be very short. The most advanced chip designs can perform all analytical functions—sampling, sample pretreatment; separation, dilution, and mixing steps; chemical reactions; and detection—in a single integrated microfluidic circuit. Lab-on-a-chip systems allow designers to create small, portable, rugged, low-cost, and easy-to-use diagnostic instruments that offer high levels of capability and versatility. Microfluidics—fluids flowing in microchannel makes possible the design of analytical devices and assay formats that would not function on a larger scale.

Lab-on-a-chip technologies attempt to emulate the laboratory procedures that would be performed on a sample within a Microfabricated structure. The most successful devices have been those that operate on fluid samples. A large number of chemical processing, purification, and reaction procedures have been demonstrated on these devices. Some degree of monolithic integration of chemical processes has been demonstrated to produce devices that perform a complete chemical measurement procedure. These devices are based upon accepted laboratory procedures of analysis and thus are able to accommodate more complex sample matrices than conventional chemical sensing.

Recent advances in molecular and cell biology have been produced in great part as a result of the development of rapid and efficient analytical techniques. Due to miniaturization and multiplexing, techniques like gene chip or biochip enable the characterization of complete genomes in a single experimental setup. PCR (Polymerase chain reaction) is a molecular biology method for the in-vivo amplification of nuclear acid molecules. The PCR technique is rapidly replacing other time consuming and less sensitive techniques for identification of biological species and pathogens in forensic, environmental, clinical and industrial samples. Among the biotechniques, PCR has become the most important analytical step in life sciences laboratories for a large number of molecular and clinical diagnostics. Important developments made in PCR technology like real-time PCR, have led to rapid reaction processes compared to conventional methods. During the past several years, microfabrication technology has been expanded to the miniaturization of the reaction and analysis system such as PCR analysis with the intention of further reducing analysis time and consumption of reagents.

In most PCR's available now, instantaneous temperature changes are not possible because of sample, container, and cycler heat capacities, and extended amplification times of 2 to 6 hours result. During the periods when sample temperature is making a transition from one temperature to another, extraneous, undesirable reactions occur that consume important reagents and create unwanted interfering compounds.

LTCC is used in packaging semiconductor devices. This system enables integration of electrical and structural function. The layer by layer fabrication sequence in LTCC fabrication process enables creation of three dimensional structures with integrated electrical elements with ease. In addition, it is cheaper to process when compared to silicon processing. A chip is fabricated on a ceramic substrate like LTCC (Low Temperature Co-fired Ceramic) enables integration of mechanical and electrical elements easily and cheaply.

Use of a portable computing platform like PDA gives the system enough computing power to control the electronics and provide a rich yet simple user interface to display the data. It also makes the entire system modular and hence enables easy upgradation the system with minimal cost to the user.

OBJECTS OF INVENTION

The principle objective of the instant invention is to develop a hand held micro PCR device.

Yet another object of the present invention is to develop a method to monitor and control hand held micro-PCR device.

STATEMENT OF INVENTION

Accordingly, the invention provides a hand held micro PCR device comprising: a LTCC micro PCR chip comprising a heater, a reaction chamber to load a sample, a heater control to regulate the heater on basis of input received from a temperature sensor, an optical detection system to detect a fluorescence signal from the sample, and at least one communication interface to interact with other device(s); and there is also provided a method to monitor and control hand held micro-PCR device said method comprising of the steps: establishing a communication between the hand held micro PCR device and other device through a communication interface, initiating a thermal cycling process based on thermal profile values received from the other device to control an LTCC micro PCR chip, and sending an optical signal detected by optical system to the other device.

BRIEF DESCRIPTION OF THE ACCOMPANYING DRAWINGS

The invention will now be described with reference to the accompanying drawings.

DETAILED DESCRIPTION OF THE INVENTION

Figure 1:
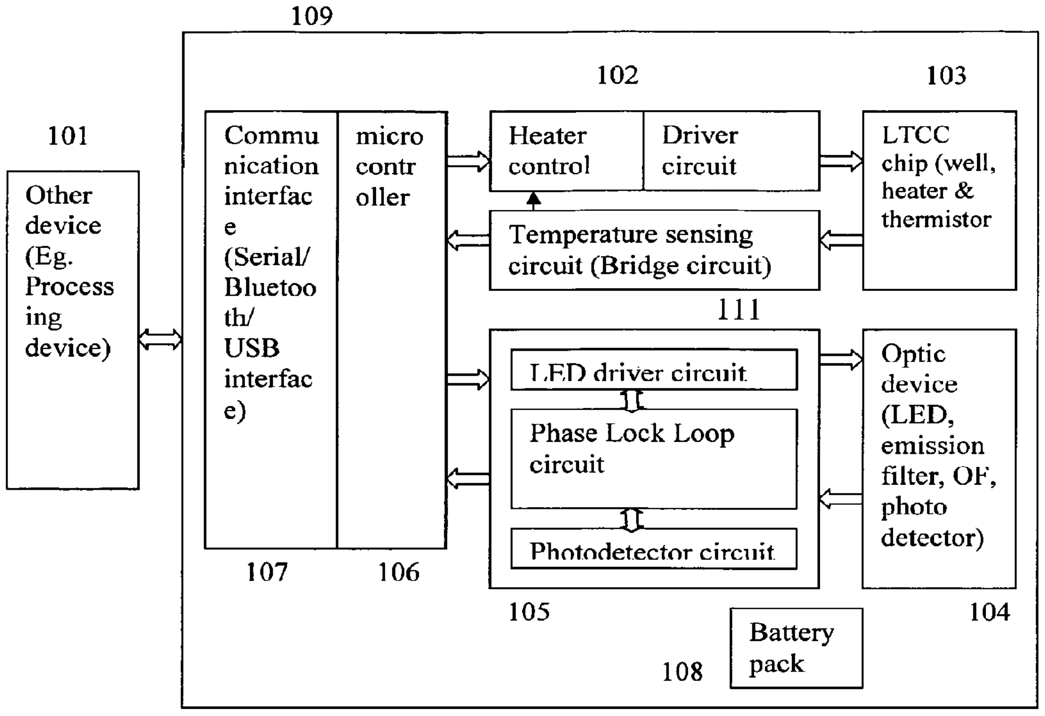
FIG. 1 shows a schematic of an embodiment of the LTCC micro PCR device according to this invention.

The present invention relates to a hand held micro PCR device comprising:

a) a LTCC micro PCR chip comprising a heater, a reaction chamber to load a sample, b) a heater control to regulate the heater on basis of input received from a temperature sensor, c) a an optical detection system to detect a fluorescence signal from the sample, and d) at least one communication interface to interact with other device(s).

In one embodiment of the present invention at least one conductor layer is provided between the heater and the reaction chamber.

In one embodiment of the present invention the reaction chamber is surrounded by conductor rings.

In one embodiment of the present invention the conductor rings are connected to the conductor layer with posts.

In one embodiment of the present invention the conductor is made of a material selected from group comprising gold, silver, platinum and palladium or alloys thereof.

In one embodiment of the present invention the temperature sensor is placed outside the chip to measure temperature of the chip.

In one embodiment of the present invention the temperature sensor is embedded in at least one layer of the chip.

In one embodiment of the present invention the temperature sensor is a thermistor.

In one embodiment of the present invention the temperature sensor is connected as one arm of a bridge circuit.

In one embodiment of the present invention the bridge circuit output is amplified before feeding it to the heater control to regulate the heater.

In one embodiment of the present invention the chip comprises a transparent sealing cap to cover the reaction chamber.

In one embodiment of the present invention the chip is disposable.

In one embodiment of the present invention the optical detection system is selected from the group comprising of a beamsplitter optical detection system, a hybrid optical detection system and bifurcated optical detection system In one embodiment of the present invention the optical system comprises a light source and a photo detector to detect a fluorescence signal from the sample.

In one embodiment of the present invention a lock-in amplifier amplifies the detected signal.

In one embodiment of the present invention the bifurcated optical system uses a bifurcated optical fiber with the light source placed at one bifurcated end (605*a*) and the photo detector placed at another bifurcated end (605*a*) of the optical fiber.

In one embodiment of the present invention the common end (605*b*) of the bifurcated optical fiber points towards the sample.

In one embodiment of the present invention the hybrid optical detection system uses optical fiber to direct light on to the sample.

In one embodiment of the present invention the hybrid optical detection system uses lenses to focus emitted beam from the sample.

In one embodiment of the present invention the communication interface is selected from the group comprising serial, USB, Bluetooth or combinations thereof.

In one embodiment of the present invention the other device collect temperature of the chip and the amplified signal from the hand held device.

In one embodiment of the present invention the other device is selected from group comprising smart phone, PDA and programmable device.

The present invention is also related to a method to monitor and control hand held micro-PCR device said method comprising of the steps:

a) establishing a communication between the hand held micro PCR device and other device through a communication interface, b) initiating a thermal cycling process based on thermal profile values received from the other device to control an LTCC micro PCR chip, and c) sending an optical signal detected by optical system to the other device.

One embodiment of the present invention, feeding the thermal profile values into the other device by a user through user interface.

In one embodiment of the present invention creating, modifying or deleting the thermal profiles through the user interface.

In one embodiment of the present invention the other device provides for authentication of the user.

In one embodiment of the present invention the other device stores a plurality of thermal profiles.

In one embodiment of the present invention the thermal profile provides for set point value and number of cycles.

In one embodiment of the present invention, maintaining the chip at a temperature and for a time determined by the set point value.

In one embodiment of the present invention, bringing the micro PCR chip temperature to room temperature by stopping the thermal cycling process.

In one embodiment of the present invention, maintaining the micro PCR chip temperature constant when the thermal cycle is paused.

In one embodiment of the present invention communicating with the other device using mobile Bluetooth serial port profile stack.

In one embodiment of the present invention plotting the thermal and optical data on a display unit of the other device.

Other device (101) are those which is capable to interact with the hand held device through any standard communication interface (107) like for example wire based (RS232 serial port, USB) or wireless (Bluetooth implementing a serial port profile) etc.

LTCC micro PCR chip is a PCR chip made of LTCC layers. This chip can be easily attached or detached from the hand held unit.

Thermal profile has the temperature and time which is the set point values as well as the count for number cycles to complete a thermal cycle process.

The Polymerase Chain Reaction (PCR) is a technique discovered to synthesize multiple copies of a specific fragment of DNA from a template. The original PCR process is based on heat stable DNA polymerase enzyme from *Thermus aquaticus* (Taq), which can synthesize a complimentary strand to a given DNA strand in a mixture containing four DNA bases and two primer DNA fragments flanking the target sequence. The mixture is heated to separate the strands of double helix DNA containing the target sequence and then cooled to allow the primers to find and bind to their complimentary sequences on the separate strands and the Taq polymerase to extend the primers into new complimentary strands. Repeated heating and cooling cycles multiply the target DNA exponentially, since each new double strand separates to become two templates for further synthesis.

A typical temperature profile for the polymerase chain reaction is as follows:

1. Denaturation at 93° C. for 15 to 30 seconds
2. Annealing of Primer at 55° C. for 15 to 30 seconds
3. Extending primers at 72° C. for 30 to 60 seconds As an example, in the first step, the solution is heated to 90-95° C. so that the double stranded template melts ("denatures") to form two single strands. In the next step, it is cooled to 50-55° C. so that short specially synthesized DNA fragments ("primers") bind to the appropriate complementary section of the template ("annealing"). Finally the solution is heated to 72° C. when a specific enzyme ("DNA polymerase") extends the primers by binding complementary bases from the solution. Thus two identical double strands are synthesized from a single double strand.

The primer extension step has to be increased by roughly 60 sec/kbase to generate products longer than a few hundred bases. The above are typical instrument times; in fact, the denaturing and annealing steps occur almost instantly, but the temperature rates in commercial instruments usually are less than 1° C./sec when metal blocks or water are used for thermal equilibration and samples are contained in plastic microcentrifuge tubes.

By micromachining thermally isolated, low mass PCR chambers; it is possible to mass-produce a much faster, more energy efficient and a more specific PCR instrument. Moreover, rapid transitions from one temperature to another ensure that the sample spends a minimum amount of time at undesirable intermediate temperatures so that the amplified DNA has optimum fidelity and purity.

Low Temperature Co-fired Ceramics (LTCC) is the modern version of thick film technology that is used in electronic component packaging for automotive, defense, aerospace and telecommunication industry. It is an alumina based glassy ceramic material that is chemically inert, bio-compatible, thermally stable (>600° C.), has low thermal conductivity (<3 W/mK), good mechanical strength and provides good hermiticity. It is conventionally used in packaging chip level electronic devices where in they serve both structural and electrical functions. The present inventors have recognized the suitability of LTCC to be used for micro PCR chip applications, and, to the best knowledge of the inventors, LTCC has not been used before for such purpose. The basic substrates in LTCC technology is preferably unfired (green) layers of glassy ceramic material with a polymeric binder. Structural features are formed by cutting/punching/drilling these layers and stacking multiple layers. Layer by layer process enables creating three-dimensional features essential for MEMS (Micro Electro Mechanical Systems). Features down to 50 microns can be readily fabricated on LTCC. Electrical circuits are fabricated by screen-printing conductive and resistive paste on each layer. Multiple layers are interconnected by punching vias and filling them with conducting paste. These layers are stacked, compressed and fired. Processing of stacks of up to 80 layers has been reported in the literature. The fired material is dense and has good mechanical strength.

FIG. 1 shows a schematic of an embodiment of the Micro PCR device indicating various components and their functions. The device comprises of a disposable LTCC Micro PCR chip (103), which has a reaction chamber to hold the sample with an embedded heater and an embedded temperature sensor for thermal cycling. The temperature sensor is a thermistor. The temperature sensor can also be placed outside the chip instead of embedding inside the chip. The temperature sensor could be any sensor capable of measuring the temperature. The LTCC Micro PCR chip (103) is interfaced to a hand held electronics unit (109) comprising of the control circuitry (102) having a heater control and driver circuit, which controls the heater based on the temperature sensor value. The temperature sensor value is fed to the heater control through a temperature sensing circuit (111). The heater control sets the chip temperature and maintains the temperature for a duration provided by a micro controller (106) as set point values. All the components on the hand held unit (109) are powered by a batter pack (108).

The hand held device (109) also houses an optical system (104) for detection of fluorescence signals from the micro PCR chip (103). This comprises light source, a circuit for controlling the light source, detector for sensing the emitted light from the sample, a circuit for amplification of the signal (from the sample). The hand held device (109) will be interfaced with other processing device (101) like USB/Bluetooth to a smartphone/PDA or any processing device for data acquisition and control.

The batteries could be a reachable battery having a port provided to recharge itself from external sources. For example the batteries could be like Nickel Cadmium, lithium ion or polymer that can supply peak current in excess of 1 A.

The hand held device also comprises at least one of the communication interface (107) to communicate with the other devices (101). The communication interface (107) can be wire based (RS232 serial port, USB) or wireless (Bluetooth implementing a serial port profile). Typically serial port profile is used for communication due it its speed and ease of implementation. The interface transfers data and instruction between the other device (101) and the microcontroller (106).

Other devices (101) here are those capable to control and monitor the hand held device. For example the other device could be a PDA, smart phone, a computer, a micro controller, or any processing device capable to communicate with the hand held device. The other device also provides a user interface to input and view data by a user. The other device referred here has the capability to run the relevant software to communicate, control and monitor the hand held device (109).

A microcontroller (106) controls the electronics on the hand held device (109) and communicates with the other device (101) through an interface. The micro controller has an analog to digital and digital to analog converter for interacting with the analog circuit i.e. the control circuit (102), Temperature sensing circuit (111) and optical circuit (105). The microcontroller (106) collects the set point values from the other device and provides it to the control circuit (102). The microcontroller also provides the temperature sensed by the temperature sensing circuit (111) and the optical data provided by the optical circuit (105) to the other device. The optical data here is the signal detected by the optical system (105).

Figure 2:
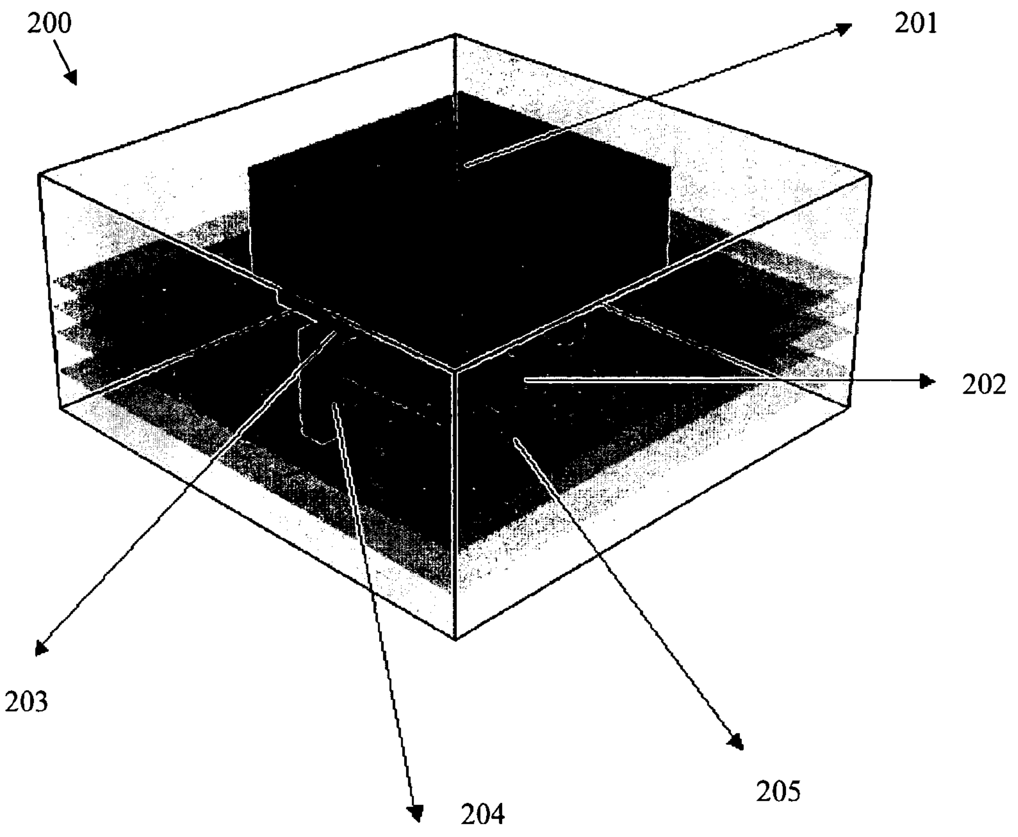
FIG. 2 shows an orthographic view of an embodiment of the LTCC micro PCR chip.

FIG. 2 shows an orthographic view of an embodiment of the micro PCR chip indicating reaction chamber (201) or well. The figure indicates the assembly of the heater (202) and a temperature sensor thermistor (203) inside the LTCC Micro PCR 15 chip. The heater conductor lines (205) and the thermistor conductor lines (204) are also indicated. These conductor lines will help in providing connection to the heater and the thermistor embedded in the hip with external circuitry.

Figure 3:
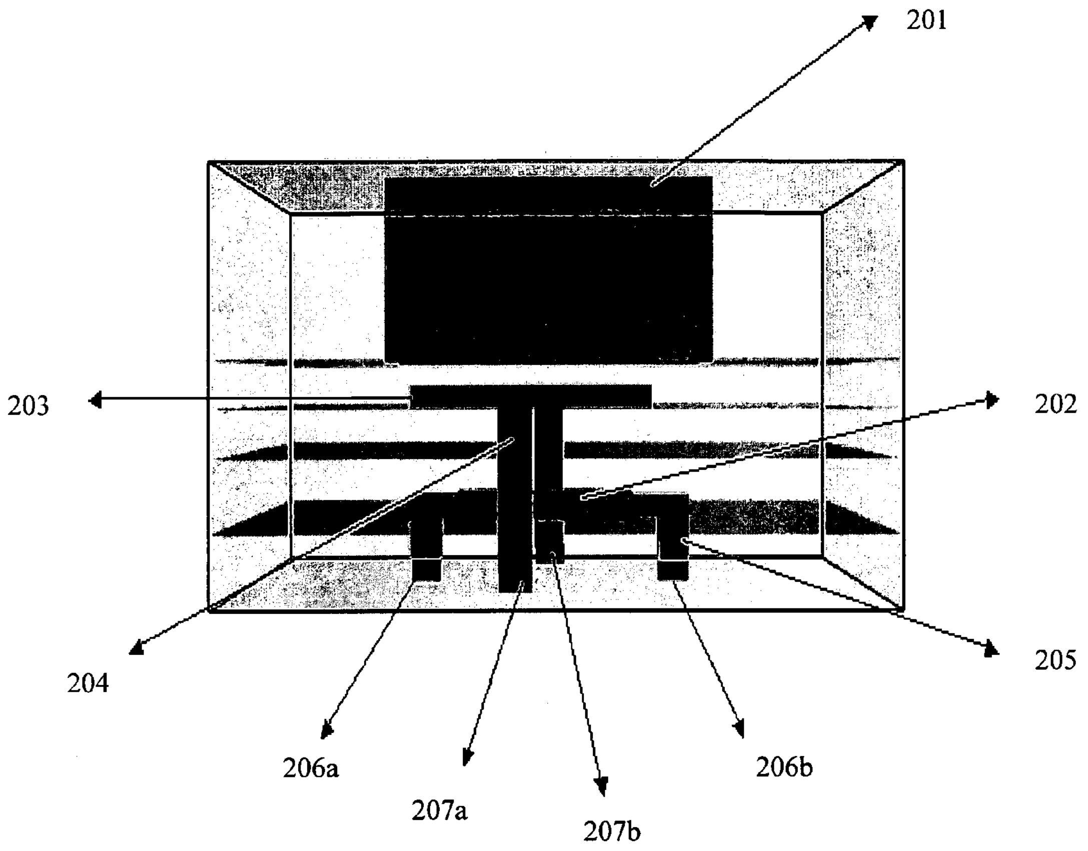
FIG. 3 shows a cross-sectional of an embodiment of the LTCC micro PCR chip.

Referring to FIG. 3 which shows a cross-sectional view of an embodiment of the LTCC micro PCR chip wherein (206*a* & 206*b*) indicate the contact pads for the heater (202) and (207*a* & 207*b*) indicate the contact pad for the thermistor (203)

Figure 4:
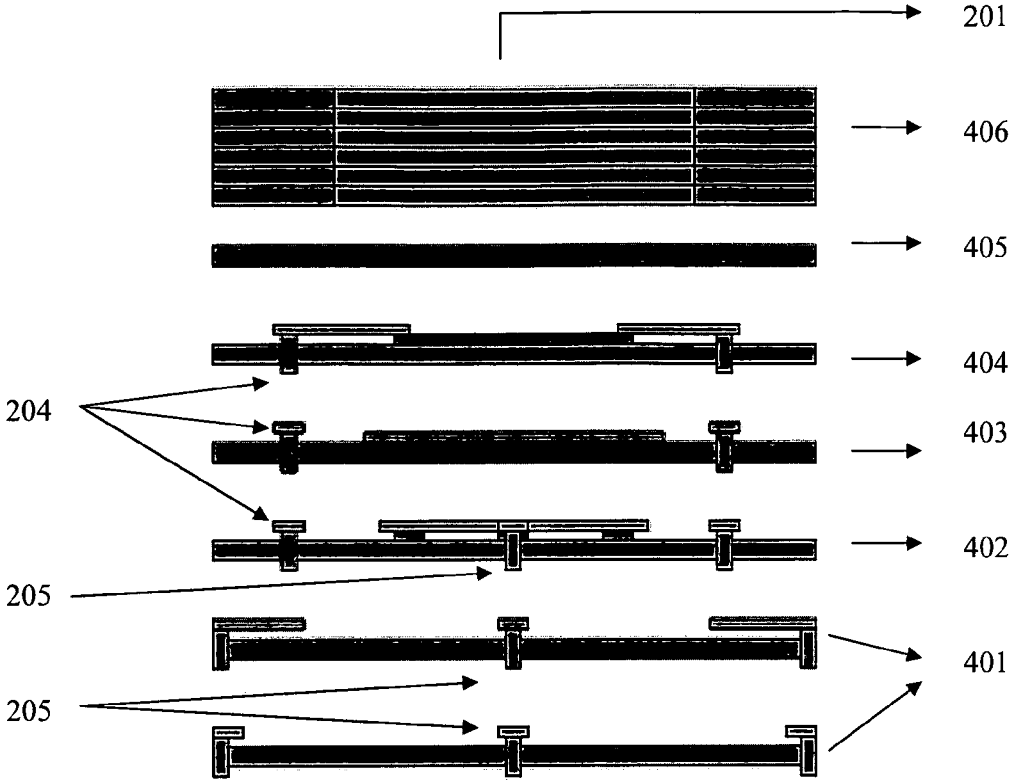
FIG. 4 shows a layer-by-layer design of an embodiment of the LTCC micro PCR chip.

Referring to FIG. 4, which shows a layer-by-layer design of an embodiment of the LTCC micro PCR chip wherein the chip, comprises of 12 layers of LTCC tapes. There are two base layers (401), three mid layers having the heater layer (402), a conductor layer (403) and a layer having thermistor (404) whereas (405) forms the interface layer to the reaction chamber (201). The reaction chamber layers (406) consist of six layers as shown. The conductor layer (403) is also provided between the heater and the thermistor layers. The heater conductor line (205) and the thermistor conductor lines (204) are also indicated. In the figure shows the conductor lines (204) is placed in either side of the thermistor layer (404). The heater design can be of any shape like “ladder”, “serpentine”, “line”, “plate”, Etc. with size varying from 0.2 mm×3 mm to 2 mm×2 mm. The size and shape of the heater can be selected based on the requirements. The requirements could be like depending on the size of the reaction chamber or the sample been tested or the material been used as a conductor layer.

The LTCC chip has a well volume of 1 to 25 μl. The heater is based on thick film resistive element that is employed in conventional LTCC packages. The thermistor system with alumina is used for fabrication of embedded temperature sensors. The measured TCR of the chip was between 1 and 2Ω/° C. The chip was fabricated on DuPont 951 green system. The thermistor layer can be placed any were in the chip or a temperature sensor can be placed outside the chip instead of thermistor inside the chip.

Figure 5:
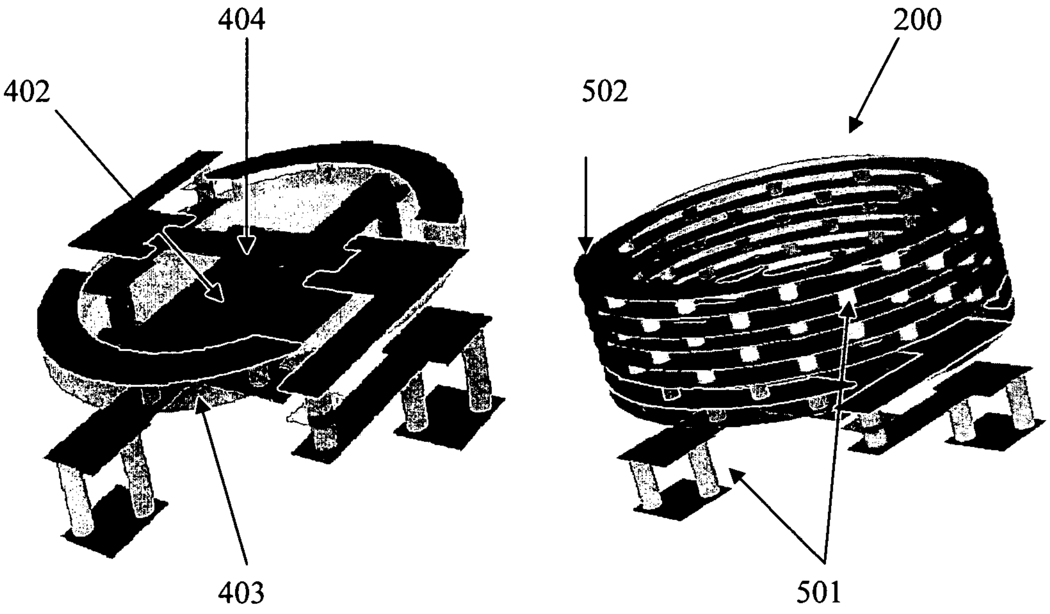
FIG. 5 shows a model of the chip reaction chamber design fabricated.

After determining the uniformity of the temperature profile with in the chip, PCR reactions were carried out on these chips. Lambda DNA fragments, *salmonella* DNA and Hepatitis B DNA has been successfully amplified using these chips. FIG. 5 shows the micro chip in 3 dimensional views showing its various connections with the heater, conductor rings, thermistor, and conducting rings (502). It also shows posts (501) that are connecting the conductor rings (502) to the conductor plate (403).

The embedded heater is made of resistor paste like CF series from DuPont compatible to LTCC. Any green ceramic tape system can be used such as DuPont 95, ESL (41XXX series), Ferro (A6 system) or Haraeus. The said embedded temperature sensor is a thermistor fabricated using a PTC (Positive Temperature Coefficient) resistance thermistor paste (E.g.: 509×D, are ESL 2612 from ESL Electroscience) for Alumina substrates. NTC: Negative Temperature Coefficient of resistance paste like NTC 4993 from EMCA Remex can also be used.

The transparent (300 to 1000 nm wavelength) sealing cap is to prevent evaporation of the sample from the said reaction chamber and is made of polymer material.

Optical Detection System (104, 105)

The optical (fluorescence) detection system comprises of an illumination source, typically an LED, filters for selection of light of appropriate wave length, optics for delivering and collecting light from the sample, and light sensor (photodiode, photomultiplier tube, phototransistor, image sensor, etc). It also comprises of circuitry (105) to drive the light source, to detect signal from the light sensor. In portable applications photodiode or phototransistor or image sensor is preferred due to it low power consumption (<1 milliW). Real time detection of PCR products employs fluorescence technique, where in a photosensitive dye (fluorophore like SYBR Green) present in the PCR mixture absorbs light of certain wave length and emits at a higher wavelength (470 nm & 520 nm for SYBR Green). Typically the emitter light intensity progressively increases or decreases with the successful progress of the PCR. Monitoring the change in the emitted intensity imparts real time detection capability for the PCR device. Coupling and collection of light from the PCR sample can be achieved in multiple ways. The following methods can be employed in the system Bifurcated optical detection system using bifurcated optical fiber (605) (multi mode plastic or silica fiber or fiber bundles) having bifurcated end (605*a*) and a common end (605*b*). One of the bifurcated ends (605*a*) is for incidence of light from LED (601) on to the sample and the other end to incident light on to a photo detector (602). The common end (605*b*) directs light on to the sample. This method employs optics for coupling light to and from fiber in addition to filters for wave length selectivity.

Figure 19:
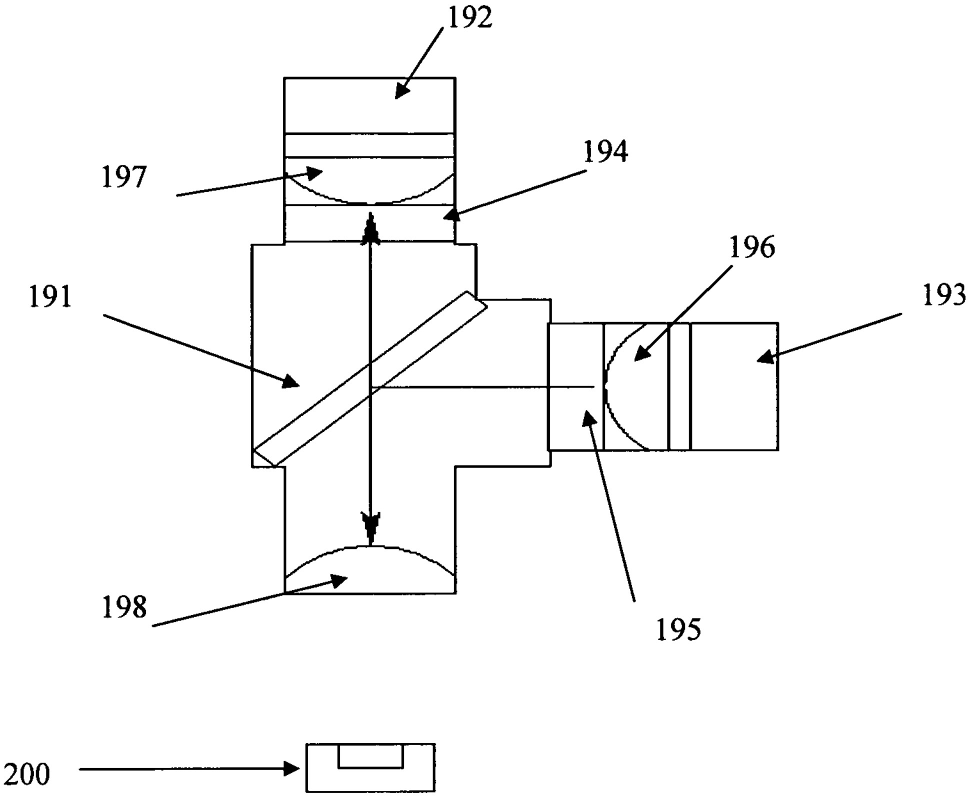
FIG. 19 shows a beamsplitter optical detection system using beamsplitter.

A beamsplitter optical detection system using beam splitters, lenses and filters for focusing light to sample and detection. FIG. 19

Figure 20:
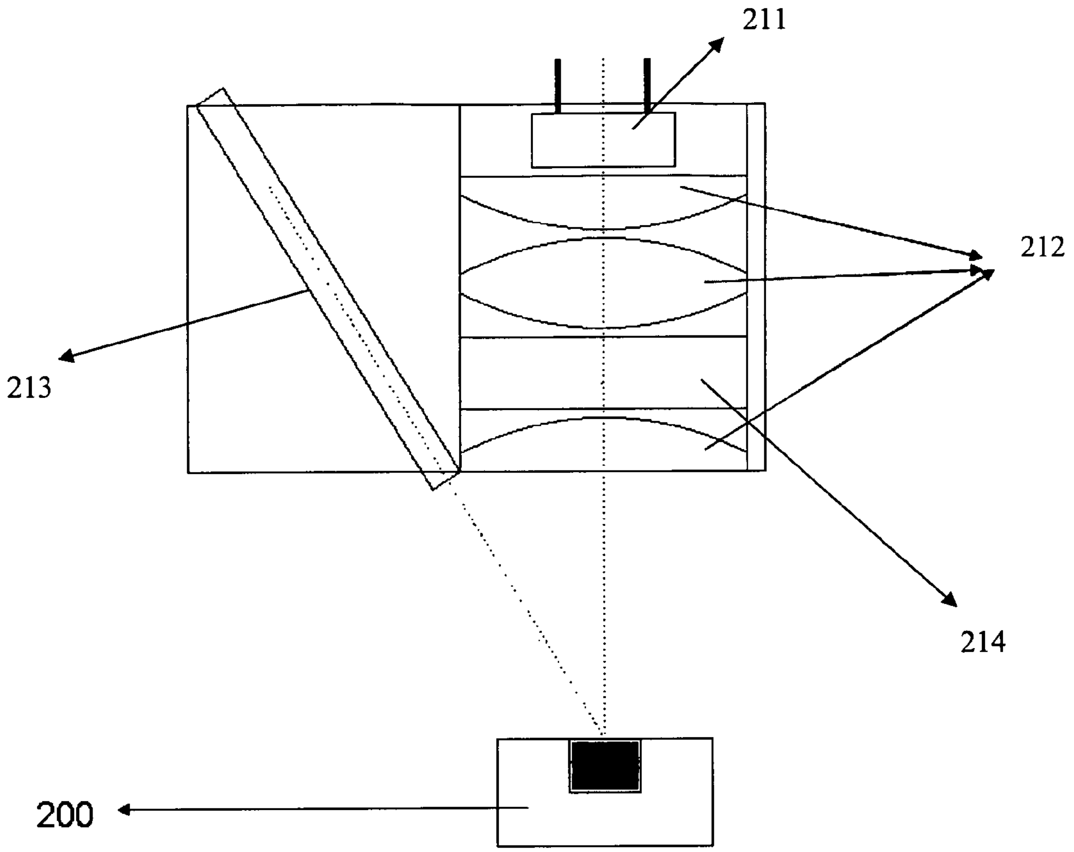
FIG. 20 shows a hybrid optical detection system.

Hybrid optical detection system employing optical fiber for illumination and direct detection using focusing lens, filter and detector. FIG. 20

Figure 6:
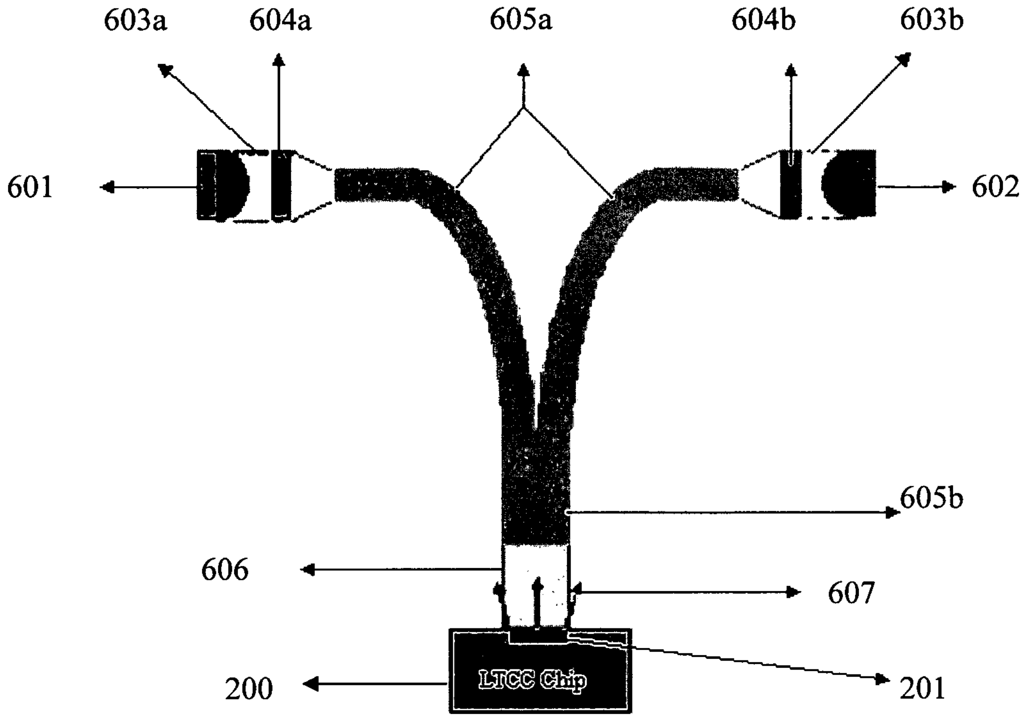
FIG. 6 shows a bifurcated optical detection system using bifurcated optical fiber.

FIG. 6 shows an embodiment of the optical system which is preferred for a PCR device in accordance with the present invention. Figure shows the configuration with bifurcated optical fiber (605) comprising of an excitation source of an LED (601) at one end of the bifurcated end (605*a*) and the fluorescence detected by a Photo detector (602) at another bifurcated end (605*a*). The LED (601) and Photo detector (602) are coupled to the bifurcated end (605*a*) of the optical fiber and the common end (605*b*) looking into the reaction chamber (201) of the LTCC chip (200). The figure also shows a filter (604*a*) coupled to the LED (601) and a filter (604*b*) coupled to the photo detector (602) by couplers (603*a* & 603*b*) respectively.

Figure 7:
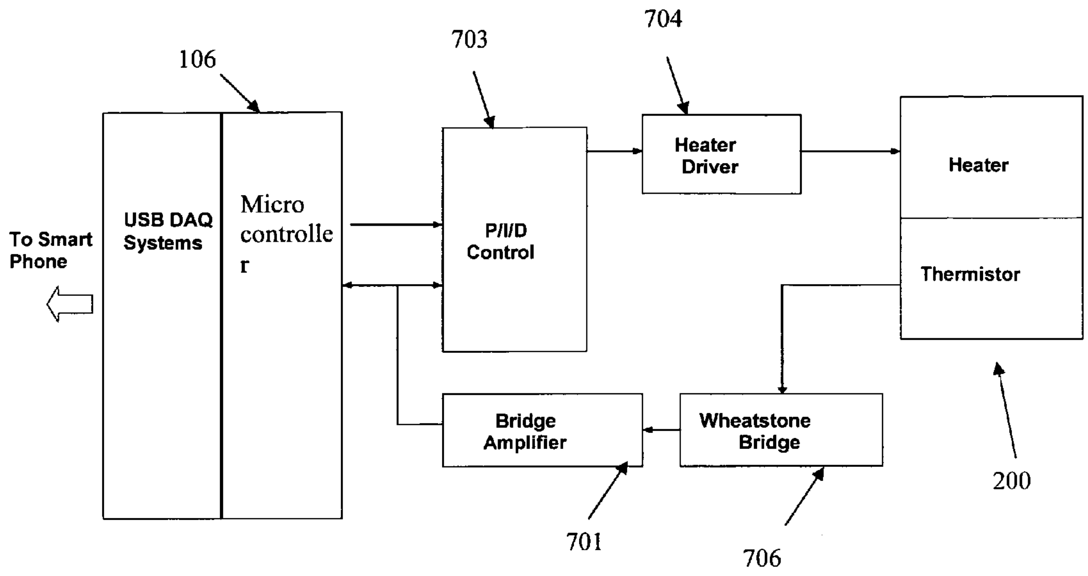
FIG. 7 shows a block diagram of the circuit controlling the heater and temperature sensor.

The output signal from the detector (602) is amplified (in-situ in photomultiplier tube, avalanche photodiode) using an amplifier circuit (701) as in FIG. 7 before being sent to heater controller. An example of amplifier circuit is phase locked loop (PLL) circuit (lock-in amplifier). In this circuit the illumination is pulsed at a predefined frequency (typically in 10 Hz to 500 kHz range). The output signal (fluorescence signal) processing circuit locks on to the same frequency and generates a proportional direct current (DC) that is amplified, converted to a voltage and further amplified sent to the microcontroller (106). This circuit enhances signal to noise ratio of the signal and eliminates frequency related noise in the signal. The lock-in circuit is based on balanced modulator/demodulator (like AD 630 JN from Analog Devices).

FIG. 7, shows a block diagram of the circuit controlling the heater and thermistor wherein the thermistor in the LTCC Micro PCR Chip (200) acts as one of the arms in the bridge circuit (706). Even when the temperature sensor is placed out side the chip it can be connected to one of the arms of the bridge circuit. The amplified output of the bridge from the bridge amplifier (701) is given as input to the PID controller (703), where it is digitized and the PID algorithm provides a controlled digital output. The output is again converted back to analog voltage and this drives the heater using a power transistor present in the heater driver (704).

The analog circuit implemented for the heater control (703) employs a P or PI or PD or PID (Proportional Integral Derivative) or can be a simple on/off control based on the output from the thermistor. The temperature sensor is a part of a circuit which detects the change in temperature. In this figure an example of thermistor is considered for the temperature sensor wherein it is made a part of wheatstone bridge circuit (706). Change in the thermistor resistance due to heating or cooling results in a finite output voltage from the circuit. This voltage is related to the temperature of the well on the LTCC chip. The measured voltage is used to determine if the heater is to be turned on or off. The heater is supplied with a preset power determined by maximum temperature to be attained in the well (on the LTCC chip). To account for the resistance variation in the heater and thermistor (~20% for optimized chip), a self calibration circuit has been developed and is being implemented in the hand held. The circuit compensates for the changes in the resistances by using a commercial thermistor (PT100) exposed to the ambient.

The heater control circuit is managed by a microcontroller. The microcontroller is programmed to run the desired thermal profile through the communication interface. The program controls the heater control circuit (102) to run the desired profile on the LTCC chip. A Bluetooth interface has been tested for controlling the microcontroller using software running on a PDA (iPaq running WincowsCE). Development of software for Bluetooth communication and development of GUI (Graphical User Interface) is being implemented in the hand held device (109). The method of controlling the heater and reading the temperature sensor value disclosed here is only an example. This should not be considered as the only way to controller or the limitation. Other means and method to control the heater and reading the thermistor value is well applicable to the instant discloser.

The other device enables users to create thermal profiles for the PCR through a GUI (Graphical User Interface). The thermal profiles are transferred to the microcontroller through the communication interface (107). The thermal profile comprises set point values (Temperature and time) and the number of cycles. The temperature sensor data and the optical detection data from the microcontroller is sent to the other device and displayed on it. The computer will also evaluate the data and display the result of the reaction. The portable computer runs on an operating system like Windows CE/Mobile, Palm OS, Symbian, Linux. In still another embodiment it is possible that only the set point values are sent to the hand held device and the number of cycles are monitored by the other device. The microcontroller achieves the set point values sent from a thermal profile by the other device.

Typically the PCR product is analyzed using gel electrophoresis. In this technique, DNA fragments after PCR are separated in an electric field and observed by staining with a fluorescent dye. A more suitable scheme is to use a fluorescent dye that binds specifically to double strand DNA to monitor the reaction continuously (real-time PCR). An example of such a dye is SYBR GREEN that is excited by 490 nm blue light and emits 520 nm green light when bound to DNA. The fluorescence intensity is proportional to the amount of double stranded product DNA formed during PCR and hence increases with cycle number.

An example below explains different possibilities that can be achieved using the hand held device (109) with other device. The other device considered in this example is a PDA/Smartphone.

Figure 15:
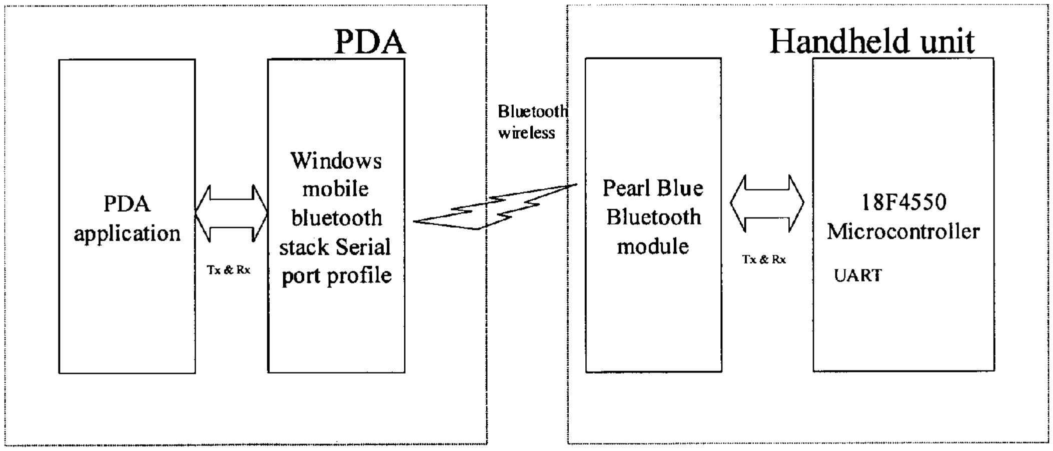
FIG. 15 shows an overview of the Personal Digital Assistant (PDA) application communicating with the hand held unit.

The targeted PDA/Smartphone application runs on a Windows mobile 5 platform. It uses windows mobile Bluetooth serial port profile (SPP) stack to communicate with the hand held unit. The hand held unit comprises of a bluetooth module, which interfaces with the microcontroller through UART (Universal asynchronous receive and transmit) port for the data communication. The core functionality of the application is to control and monitor the thermal cycling process of the hand held unit though various stored thermal profiles. It also has functionalities like two level access control; data plotting, creating thermal profiles, etc. FIG. 15 illustrates the communication method between the application and the hand held unit.

PDA Application

Figure 17:
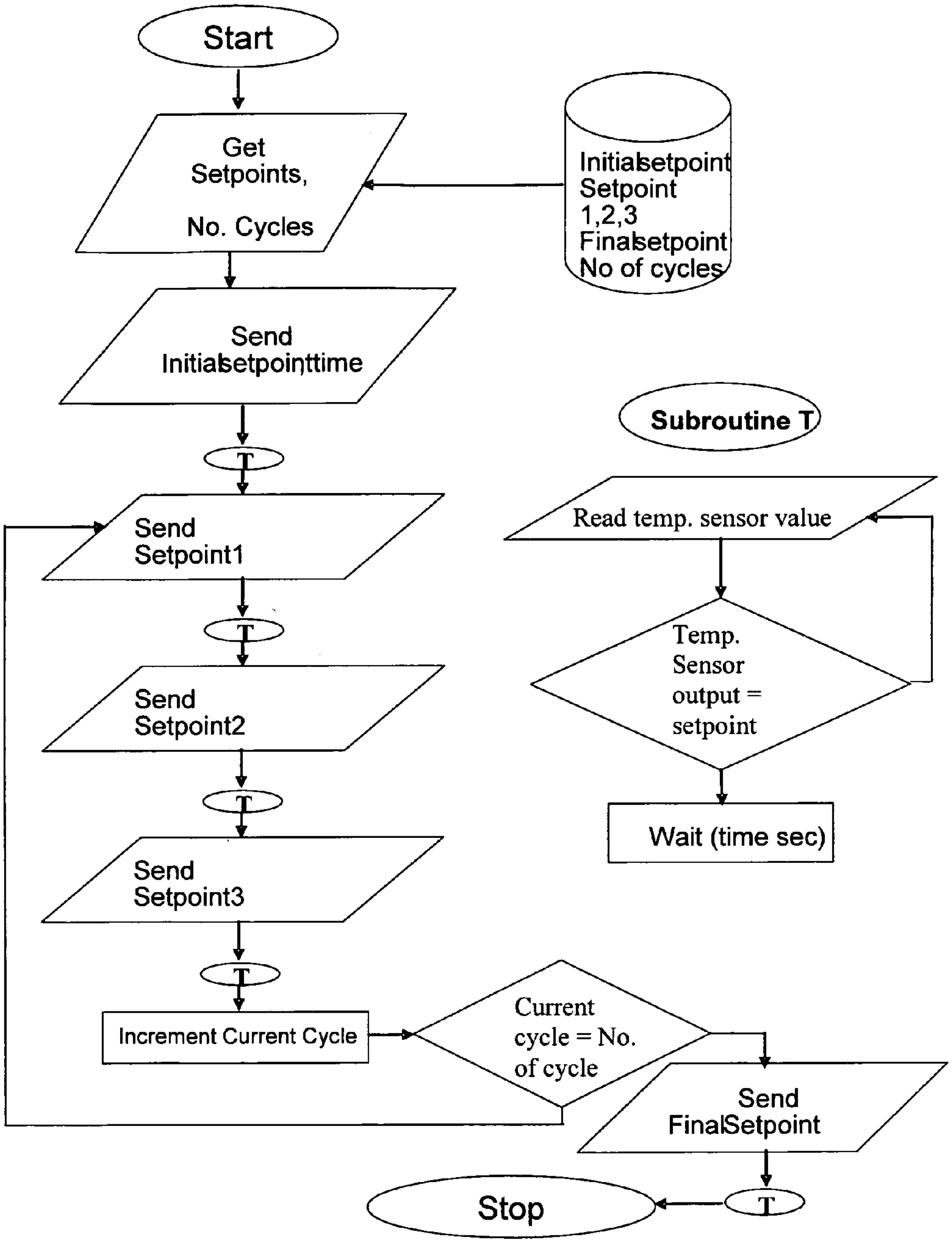
FIG. 17 shows a flowchart for the thermal cycling program running in the PDA.
Figure 18:
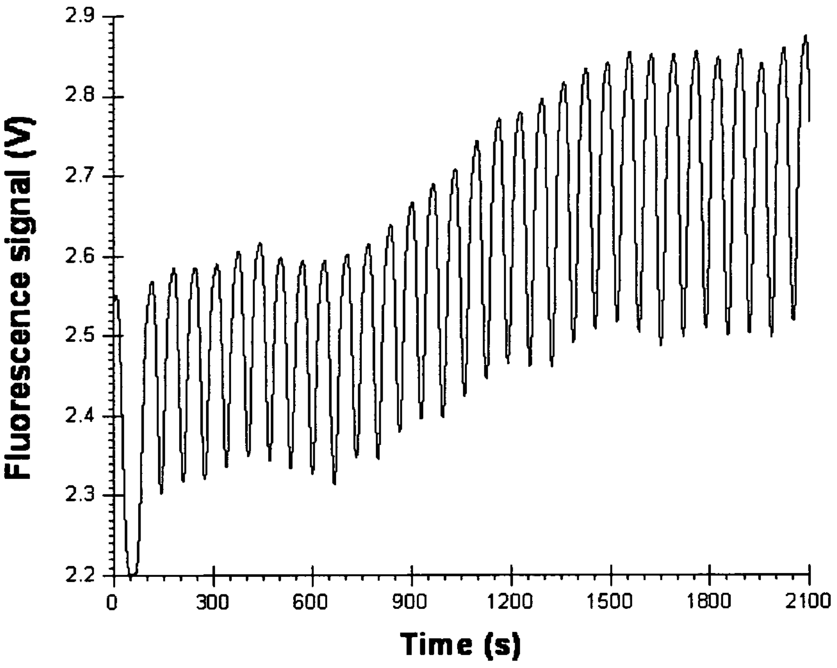
FIG. 18 shows realtime fluorescence signal of amplified HBV DNA using microchip.

The PDA application program accepts the input data which includes set point values (temperature and time) and the number of cycles. The set point values are transferred to the hand held unit through a Bluetooth connection and waits for the hand held unit's response. On attaining the set point value the hand held unit communicates the same to the PDA which sends the next set of instructions (FIG. 17). The PDA also receives data from the hand held (temperature and optical data) and displays it. To communicate and execute the instructions sent by PDA, the hand held has a micro controller with embedded program that enables Bluetooth communication and control of analog circuits. In addition, the program on the microcontroller continuously sends temperature and optical data to the PDA.

The PDA application has 4 modules:

1. Access control
2. GUI
3. Data processing and communication

Access Control:

1. This module allows users to login to the application.
2. It has a login screen with User name & Password.
3. There are two levels of access controls a. Administrative b. User
4. Administrator has the following powers:
   a. Create users and user folders
   b. Create thermal profiles
   c. Connect to/Change hand held device (109)
5. Users once logged in with their Usernames & Passwords, have powers to execute the application, view and store the data pertaining to their session.

GUI

1. GUI module provides screens for:
   a. Administrators to enter different Setpoints (Temperature & Time) and create/delete/modify thermal profiles.
   b. Create/delete Users and user folders.
   c. Change of handheld device.

i. The application uses the bluetooth stack to detect bluetooth devices in range. After detection, it displays all the available devices in range. Administrator will select the hand held device and the application requests the bluetooth stack to pair with the hand held device (109). After pairing it will store the paired device information for future use.

d. Start, stop, restart and pause the application.

e. A log window, which shows the data transmitted and received by the application.

2. GUI module has a screen to plot the thermal & optical data collected from the hand held unit.

Data Processing Module

The data processing module has the following functionality:

1. Data conversion
2. Communication algorithm.

Data Conversion:

1. Data is collected from a thermal profile selected by the user.
2. The following is a typical thermal profile:

Initial Setpoint $$\left.\begin{array}{l}\text{Setpoint 1}\\\text{Setpoint 2}\\\text{Setpoint 3}\end{array}\right\}\text{Number of cycles}$$

Final Setpoint.

3. As Setpoint contains values contains Temperature and Time, The temperature values are then converted to voltage values by using a formula:

$$V = \frac{t - x}{y}$$

Where V is voltage and t is temperature. x & y are predefined constants.

4. The voltage values thus obtained will be converted to 10-bit hexadecimal (base-16) values by using the formula:

$$\frac{V}{V_{supply}} * 1023$$

Where V is voltage.

5. The time values (in seconds) are converted to hexadecimal (hex) value.
6. The thermal data collected from the hand held unit will be converted from hexadecimal value to voltage for plotting using the formula:

$$\frac{Hex}{1023} * V_{supply}$$

7. Voltage is again converted back to temperature:

$$t = V^*y + x$$

8. The optical data collected will be converted to voltage and will be directly sent to plotting, Data Communication:

The data communication module talks to the windows mobile bluetooth stack. The following protocols are followed during the communication.

Start:

The start button provided by the application program starts the thermal cycling process. The application requests the bluetooth stack to establish a wireless serial port connection with the hand held unit. After receiving the acknowledgement, The PDA starts communicating with Hand held unit.

Stop/Pause/Continue

Stop command will stop the thermal cycling and indicate the hand held unit to bring down the chip's temperature to room temperature—this process cannot be restarted. Pause will hold the chip's temperature to current running temperature. This can be revoked by continue command Use of a portable computing platform like PDA gives the system enough computing power to control the electronics and provide a rich yet simple user interface to display the data. It also makes the entire system modular and hence enables easy upgradation the system with minimal cost to the user.

The invention provides a marketable hand held PCR device for specific diagnostic application. The program running on the other device provides a complete hand held PCR system with real time detection and software control.

Figure 14:
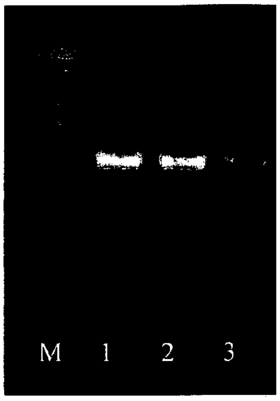
FIG. 14 shows time taken for amplifying Hepatitis B Viral DNA using LTCC chip

By reducing thermal mass and improved heating/cooling rates using the device, the time taken from 2 to 3 hours to finish a 30 to 40-cycle reaction, even for a moderate sample volume of 5-25 μl, was reduced to less than 30 minutes. FIG. 14 shows the time taken for amplifying Hepatitis B Viral DNA using LTCC chip of instant invention. The PCR was run for 45 cycles and were able to achieve amplification within 45 minutes indicated as (1) in FIG. 14. Further, the amplification was observed when the PCR was run for 45 cycles in 20 minutes (2) and 15 minutes (3) also. Conventional PCR duration for HBV (45 cycles) would take about 2 hours.

Miniaturization allows accurate readings with smaller sample sizes and consumption of smaller volumes of costly reagents. The small thermal masses of Microsystems and the small sample sizes allows rapid low-power thermal cycling increasing the speed of many processes such as DNA replication through micro PCR. In addition, chemical processes that depend on surface chemistry are greatly enhanced by the increased surface to volume ratios available on the micro-scale. The advantages of micro fluidics have prompted calls for the development of integrated microsystem for chemical analysis.

The Micro chip translated into a hand held device (109), thereby removes the PCR machine from a sophisticated laboratory, thus increasing the reach of this extremely powerful technique, be it for clinical diagnostics, food testing, blood screening at blood banks or a host of other application areas.

Existing PCR instruments with multiple reaction chambers provide multiple DNA experiment sites all running the same thermal protocol and hence are not time efficient. The need arises, to minimize reaction time and intake sample volume.

Instant PCR is designed in future, could have an array of devices with very quick thermal response and highly isolated from the adjacent PCR chips to be able to effectively and independently run multiple reactions with different thermal protocols with minimum cross talk.

Figure 12:
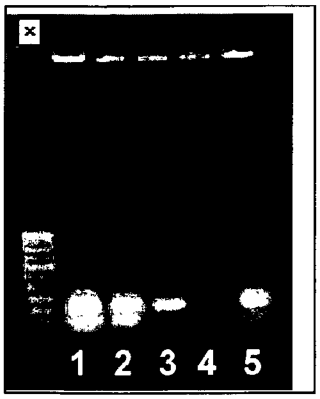
FIG. 12 shows an image of the gel of the amplification of direct plasma PCR for 16S ribosomal unit of *salmonella.*

The analysis or quantification of the PCR products is realized by practical integration of a real-time fluorescence detection system. This system could also be integrated with quantification and sensing systems to detect diseases like Hepatitis B (FIG. 12), AIDS, tuberculosis, etc. Other markets include food monitoring, DNA analysis, forensic science and environmental monitoring.

Figure 8:
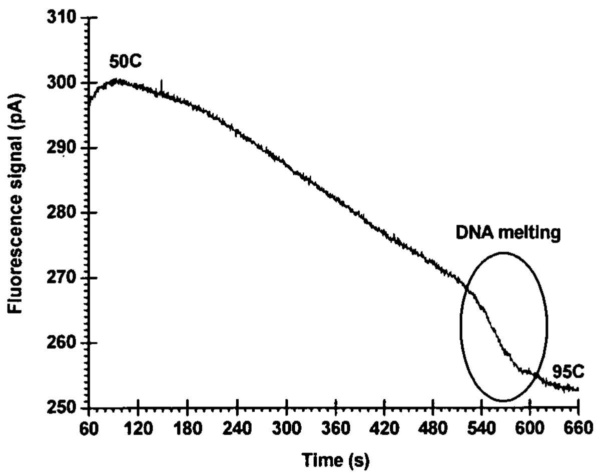
FIG. 8 shows melting of lambda-636 DNA fragment on chip using the integrated heater/thermistor, controlled by the hand held unit.

FIG. 8 shows a comparative plot of the melting of λ-636 DNA fragment on chip using the integrated heater and thermistor.

Figure 9:
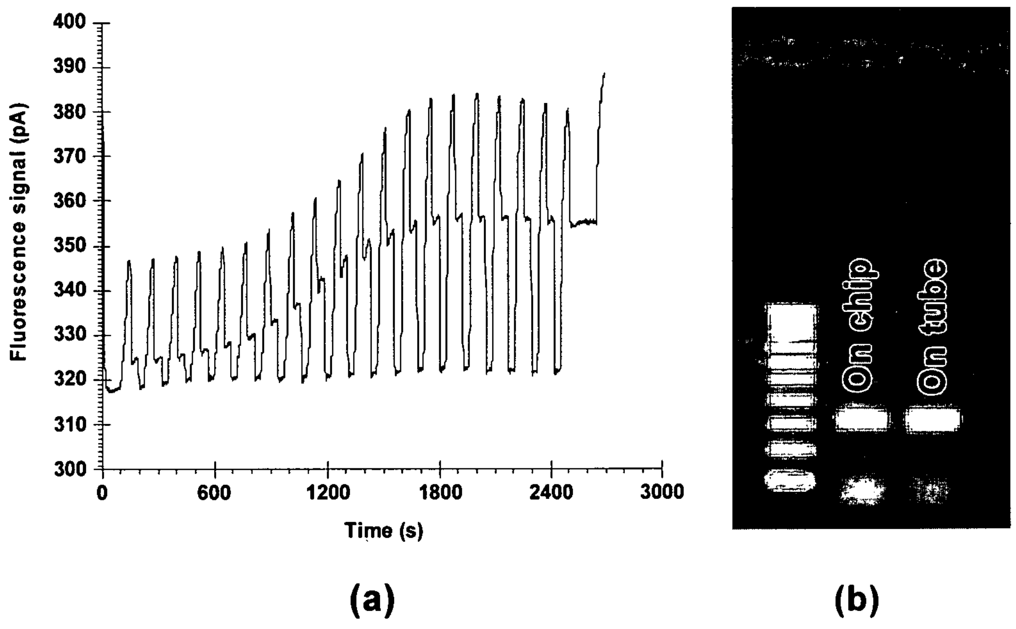
FIG. 9 shows PCR amplification of lambda-311 DNA fragment on chip. (a) Realtime fluorescence signal from the chip; (b) Image of the gel confirming the amplification product.

FIG. 9 shows the increase in fluorescence signal associated with amplification of λ-311 DNA. The thermal profile was controlled by the hand held unit and the reaction was performed on a chip (3 μl reaction mixture and 6 μl oil). The fluorescence was monitored using conventional lock-in amplifier.

Figure 13:
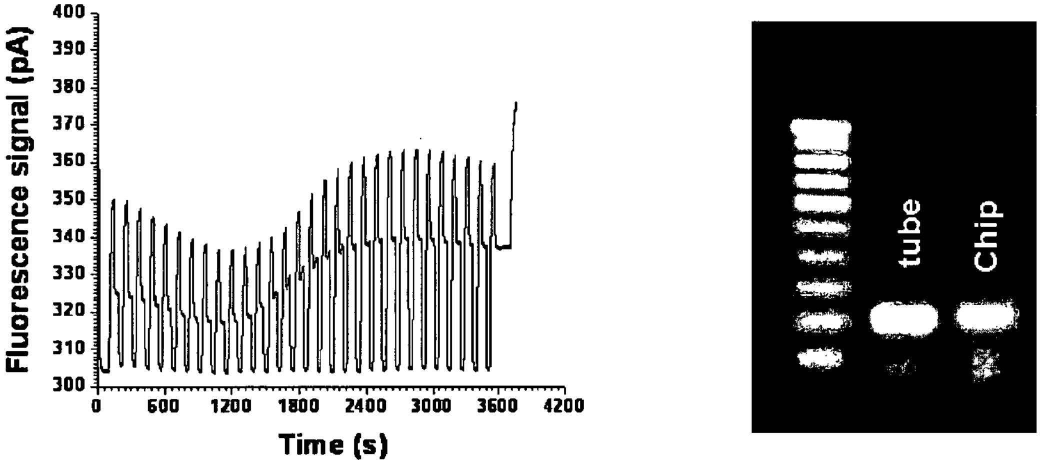
FIG. 13 shows PCR amplification of gene of *Salmonella* using microchip. (a) Realtime fluorescence signal from the chip; (b) Image of the gel confirming the amplification product

Instant invention also provides for diagnostic system. The procedure adopted for developing the diagnostic system has been to initially standardize thermal protocols for a couple of problems and then functionalize the same on the chip. Primers designed for 16S ribosomal DNA amplified ~300-400 bp fragment from *E. coli* and *Salmonella* while the primers for the stn gene amplified ~200 bp fragment from *Salmonella typhi*. The products obtained were confirmed by SYBR green fluorescence detection as well as agarose gel electrophoresis. FIGS. 9 and 13 shows the gel picture of the amplified λ-311 DNA and *salmonella* gene using micro-chip.

Thermal profile for amplification of λ-311 DNA:
Denaturation: 94° C. (90 s)
94° C. (30 s)-50° C. (30 s)-72° C. (45 s)
Extension: 72° C. (120 s)

Thermal profile for amplification of *Salmonella* gene:
Denaturation: 94° C. (90 s)
94° C. (30 s)-55° C. (30 s)-72° C. (30 s)
Extension: 72° C. (300 s)

PCR with Processed Blood and Plasma

Figure 10:
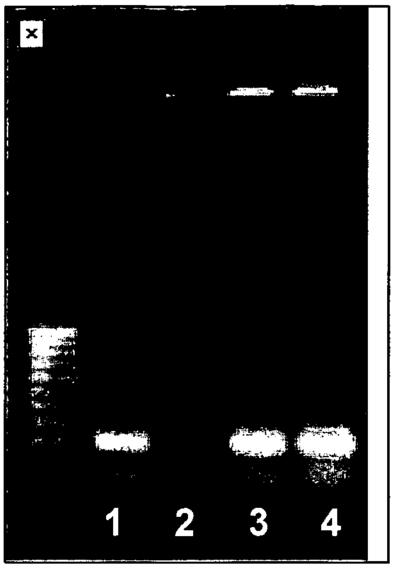
FIG. 10 shows an image of the gel of the amplification of processed blood and plasma PCR for 16S ribosomal unit of *salmonella.*
Figure 11:
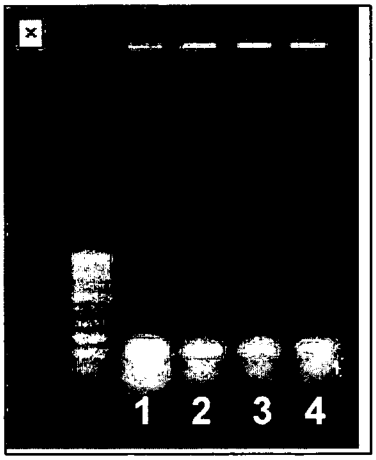
FIG. 11 shows an image of the gel of the amplification of direct blood PCR for 16S ribosomal unit of *salmonella.*

Blood or plasma was treated with a precipitating agent that can precipitate the major PCR inhibitory substances from these samples. The clear supernatant was used as a template. Using this protocol amplifications were obtained for ~200 bp fragment from *Salmonella typhi* (FIG. 10). In FIG. 10, gel electrophoresis image shows 1. control reaction,
2. PCR product—blood without processing,
3. PCR product—processed blood
4. PCR product—processed plasma Blood Direct PCR Buffer A unique buffer has been formulated for direct PCR with blood or plasma samples. Using this unique buffer system direct PCR amplification with blood & plasma has been achieved. With this buffer system, amplification has been obtained up to 50% for blood & 40% for plasma (see FIGS. 11 and 12) using LTCC chip of instant invention. In FIG. 11, gel electrophoresis image shows 1. PCR product—20% blood,
2. PCR product—30% blood,
3. PCR product—40% blood,
4. PCR product-50% blood; and in FIG. 12, gel electrophoresis image shows, 1. PCR product—20% plasma,
2. PCR product—30% plasma,
3. PCR product—40% plasma,
4. PCR product—50% plasma,
5. control reaction The unique buffer comprises a buffer salt, a chloride or sulphate containing bivalent ion, a non-ionic detergent, a stabilizer and a sugar alcohol.

Figure 16:
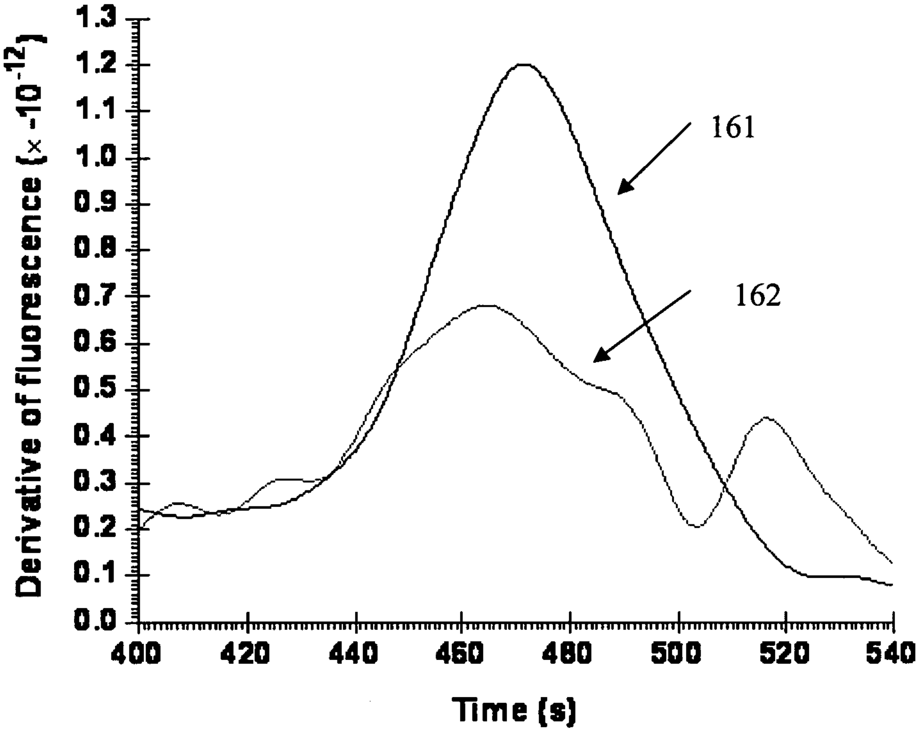
FIG. 16 shows a melting curve obtained by using a LTCC chip for derivative of the fluorescence signal for melting of λ-311 DNA.

FIG. 16 shows melting curve of LTCC chip for derivative of the fluorescence signal for melting of λ-311 DNA. The figure also provides a comparison between the instant invention (161) and the conventional PCR device (162).

Sharper peak: peak value/width (x axis)@half peak value=1.2/43

Shallower peak: peak value/width (x axis)@half peak value=0.7/63

Higher ratio indicates a sharper peak. Also in the graph, the y-axis is the derivative (slope of the melting curve), higher slope indicates sharper melting.

FIG. 19 shows description of an embodiment of the optic system with beam splitter which could be adopted in the hand held device. The fluorescence detection system comprises of a LED light source (193), lens (196) to focus light, a band pass filter (195) for selecting specific wavelength of light, a beam-splitter (191), a lens (198) to focus incident beam and signal from the sample loaded onto the chip (200), a bandpass filter (194) for selecting specific wavelength of light, focusing lens (197) and a photodetector (192).

FIG. 20 shows description of an embodiment of the hybrid optic system incorporating optical fiber and lenses. This fluorescence detection system comprises of a LED light source not shown in the figure with a band pass filter for selecting specific wavelength of light coupled to an optical fiber (213). Optical fiber directs the light on to the sample. Optionally suitable lens can be used to focus light coming out of the optical fiber on to the sample. Lenses (212) are used to calumniate emitted beam from the sample loaded onto the chip (200). A bandpass filter (214) for selecting specific wavelength of emitted light and focusing lens (212) to focus it on to a photodetector.

We claim:

1. A polymerase chain reaction (PCR) device comprising:
- a low temperature co-fired ceramic (LTCC) PCR chip comprising:
  - a heater and a reaction chamber configured to hold a sample;
  - a plurality of thermal conductor rings surrounded by and physically separate from the reaction chamber;
- a heater control interfaced with the heater;
- a temperature sensor;
- a temperature sensing circuit interfaced with the temperature sensor;
- an optical detection system to detect a fluorescence signal from the sample;
- an optical circuit interfaced with the optical detection system; and
- a communication interface that connects to an external processing device that controls and monitors the PCR device.

2. The device as claimed in claim 1, wherein the thermal conductor rings are connected to each other by a plurality of posts, the heater is embedded in a heater layer placed below a conductor layer, and the conductor layer is connected to the thermal conductor rings by a plurality of the posts.

3. The device as claimed in claim 1, wherein the temperature sensor is placed outside the chip or embedded in at least one layer of the chip to measure temperature of the chip.

4. The device as claimed in claim 1, wherein the chip comprises a transparent sealing cap to cover the reaction chamber.

5. The device as claimed in claim 1, wherein the communication interface is selected from at least one of a universal serial bus (USB) interface and a Bluetooth interface.

6. The device as claimed in claim 1, wherein the processing device is selected from the group consisting of a smart phone, a personal digital assistant (PDA), and any programmable device.

7. The device as claimed in claim 1, further comprising:
- a microcontroller electrically and communicatively coupled to the communication interface, the heater control, the temperature sensing circuit, and the optical circuit, the microcontroller programmed to:

receive input data representing a set point value from the external processing device through the communications interface, provide the set point value to the heater control, receive a temperature sensor value from the temperature sensing circuit, receive the fluorescence signal from the optical circuit, and provide the temperature sensor value and the fluorescence signal to the external processing device through the communication interface.

* * * * *